United States Patent
Ammar et al.

(10) Patent No.: US 10,226,180 B2
(45) Date of Patent: Mar. 12, 2019

(54) SYSTEM, METHOD, AND APPARATUS FOR PERFORMING HISTOPATHOLOGY

(71) Applicant: Imam Abdulrahman Bin Faisal University, Dammam (SA)

(72) Inventors: Ahmed S. Ammar, Al Khobar (SA); Manal Abdullah Alsaloum, Dammam (SA)

(73) Assignee: Imam Abdulrahman bin Faisal University, Dammam (SA)

(*) Notice: Subject to any disclaimer, the term of this patent is extended or adjusted under 35 U.S.C. 154(b) by 990 days.

(21) Appl. No.: 14/581,785

(22) Filed: Dec. 23, 2014

(65) Prior Publication Data

US 2016/0174848 A1  Jun. 23, 2016

(51) Int. Cl.
*A61B 5/00* (2006.01)
*A61B 1/00* (2006.01)
(Continued)

(52) U.S. Cl.
CPC .............. *A61B 5/0084* (2013.01); *A61B 1/00* (2013.01); *A61B 1/00009* (2013.01); *A61B 1/00082* (2013.01); *A61B 1/00135* (2013.01); *A61B 1/05* (2013.01); *A61B 1/0638* (2013.01); *A61B 1/0669* (2013.01); *A61B 1/0684* (2013.01); *A61B 1/07* (2013.01); *A61B 5/6847* (2013.01);
(Continued)

(58) Field of Classification Search
CPC ... A61B 5/0084; A61B 5/6847; A61B 5/6852; A61B 5/6868; A61B 1/00; A61B 1/00009; A61B 1/00082; A61B 1/05; A61B 1/0638; A61B 1/0669; A61B 1/0684; A61B 1/07; A61B 10/0283; A61B 10/04; G06T 7/0012
See application file for complete search history.

(56) References Cited

U.S. PATENT DOCUMENTS 5,823,940 A 10/1998 Newman
6,869,397 B2 3/2005 Black et al.
(Continued)

FOREIGN PATENT DOCUMENTS

WO    WO 2013/142366 A1    9/2013

OTHER PUBLICATIONS

Bini, et al. "Confocal Mosaicing Microscopy of Human Skin Ex Vivo: Spectral Analysis for Digital Staining to Simulate Histology-like Appearance." Journal of Biomedical Optics 16(7), 076008 (Jul. 2011).

*Primary Examiner* — Carolyn Pehlke

(74) *Attorney, Agent, or Firm* — Oblon, McClelland, Maier & Neustadt, L.L.P.

(57) ABSTRACT

A histopathology system includes an elongated, cylindrical probe having therein one or more scanners connected to a distal end of the probe and configured to capture digital images of tissue. Neuro-navigation circuitry is configured to navigate the probe to a tissue examination site. The probe is inserted into an outer casing having a mesh plate integrally formed at a distal tip of the outer casing through which a tissue is drawn. At least one balloon is attached to an inner surface of the outer casing and when inflated creates a pressure differential that draws the tissue into viewing range of the one or more scanners. At least one server is configured to digitally stain a tissue image obtained by the one or more scanners of the tissue, and match the tissue images to one or more stored tissue samples.

19 Claims, 8 Drawing Sheets

(51) Int. Cl.
    *A61B 1/05*        (2006.01)
    *A61B 1/06*        (2006.01)
    *A61B 1/07*        (2006.01)
    *A61B 10/02*     (2006.01)
    *A61B 10/04*     (2006.01)
    *H04N 5/225*    (2006.01)

(52) U.S. Cl.
    CPC ........ *A61B 10/0283* (2013.01); *A61B 5/6852* (2013.01); *A61B 5/6868* (2013.01); *A61B 10/04* (2013.01); *A61B 2505/05* (2013.01); *A61B 2576/00* (2013.01); *H04N 2005/2255* (2013.01)

(56) References Cited

U.S. PATENT DOCUMENTS

| | | | |
|---|---|---|---|
| 2002/0166946 A1* | 11/2002 | Iizuka | A61B 1/00087 250/201.2 |
| 2003/0187349 A1* | 10/2003 | Kaneko | A61B 1/00094 600/425 |
| 2011/0112410 A1 | 5/2011 | Hirota | |
| 2012/0083678 A1 | 4/2012 | Drauch et al. | |

\* cited by examiner

Patient: John Smith
ID#: 6645987
Date: 06/15/2013
Surgeon: Dr. J. Cook
Type of procedure: Cerebral Tissue Diagnosis Digital stain: IHC
Tissue match: Primary Glioblastoma
Location: Right parietal lobe
Magnification: 40X10
Tumor size: 3 cm
Notes: widespread cell necrosis and calcium deposits at tumor site Matched tissue image

FIG. 7

SYSTEM, METHOD, AND APPARATUS FOR PERFORMING HISTOPATHOLOGY

BACKGROUND

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

One of the challenges of removing diseased tissue from the body during surgery is that it can be difficult to distinguish healthy tissue from diseased tissue while in an intraoperative environment. Intraoperative frozen section procedures are often used to identify tissue.

SUMMARY

In an exemplary embodiment, a histopathology system includes an elongated, cylindrical probe having therein one or more scanners connected to a distal end of the probe and configured to capture digital images of tissue. Neuro-navigation circuitry is configured to navigate the probe to a tissue examination site. The probe is inserted into an outer casing having a mesh plate integrally formed at a distal tip of the outer casing through which a tissue is drawn. At least one balloon is attached to an inner surface of the outer casing and when inflated creates a pressure differential that draws the tissue into viewing range of the one or more scanners. At least one server is configured to digitally stain a tissue image obtained by the one or more scanners of the tissue, and match the tissue images to one or more stored tissue samples.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 7 is an exemplary illustration of a matched tissue image with amplifying information, according to certain embodiments.

DETAILED DESCRIPTION

Figure 1:
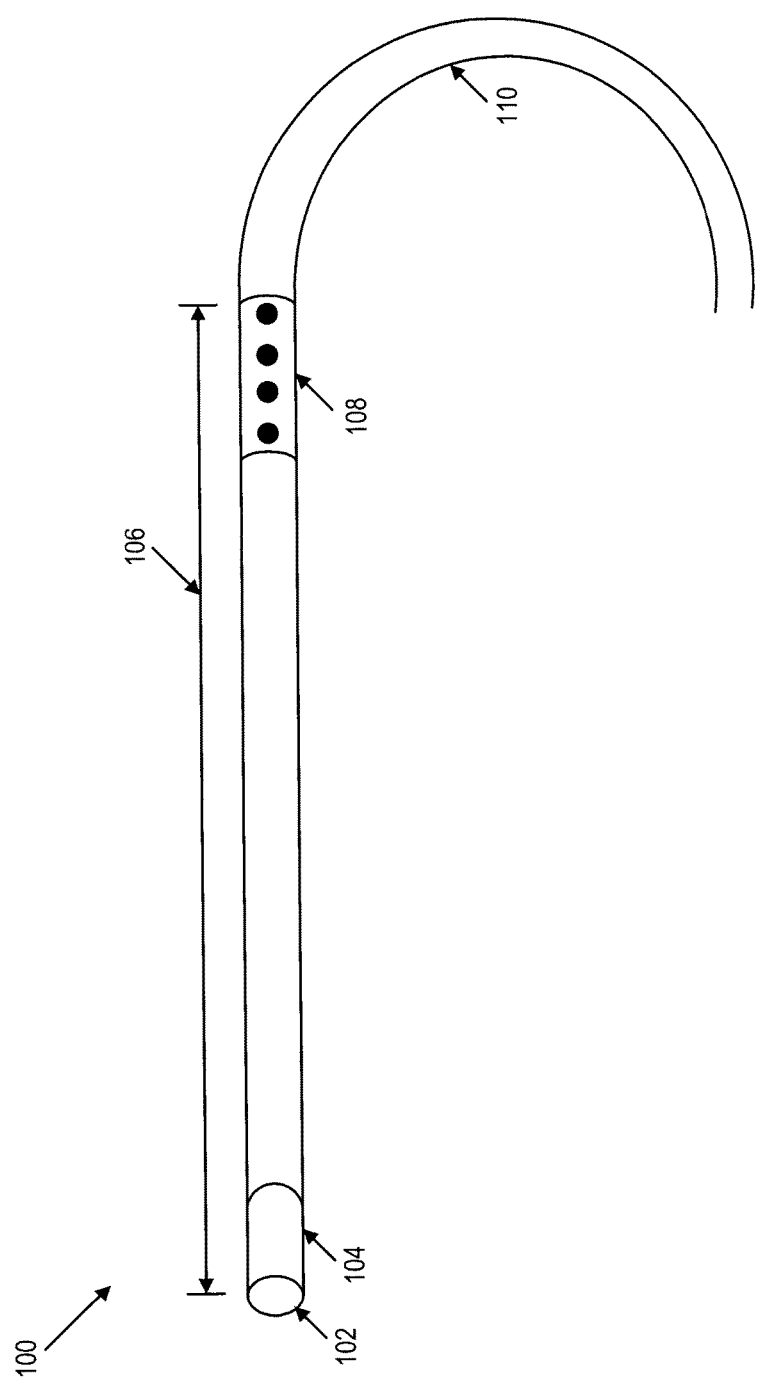
FIG. 1 is an exemplary illustration of a probe, according to certain embodiments.

In the drawings, like reference numerals designate identical or corresponding parts throughout the several views. Further, as used herein, the words "a," "an" and the like generally carry a meaning of "one or more," unless stated otherwise. The drawings are generally drawn to scale unless specified otherwise or illustrating schematic structures or flowcharts.

Furthermore, the terms "approximately," "approximate," "about," and similar terms generally refer to ranges that include the identified value within a margin of 20%, 10%, or preferably 5%, and any values therebetween.

Aspects of this disclosure are directed to a system for performing histopathology in real time. For example, while performing neurological surgery to determine if cerebral tissue includes one or more diseased or cancerous cells, a surgeon uses a probe to obtain an image of the tissue with one or more scanners, lenses, cameras, and the like, that are attached to the probe. In certain embodiments, the probe is connected to a backend system that receives the images obtained by the probe, digitally stains the tissue images, and matches the digitally stained image to one or more images in a histopathological library. In some aspects, digital staining includes digitally enhancing or modifying the images obtained by the probe to highlight features of the images, such as cell boundaries and cell components, and may assist in distinguishing between healthy and diseased tissue.

The histopathology system allows the surgeon to diagnose the tissue as healthy or diseased in real time so that the boundaries of the diseased tissue can be determined and, if necessary, the diseased tissue can be removed without having to send tissue samples to a lab to be analyzed. The histopathology system can be implemented in neurosurgery for distinguishing healthy cerebral tissue from pathological cerebral tissue. The histopathology system can also be implemented in other medical disciplines where diagnosing cells as healthy or diseased in real time may improve an outcome for a patient, such as spinal surgery, renal surgery, gynecological surgery, hepatic surgery, general surgery, and the like. The histopathology system can also be used in non-real time environments, such as during tissue examination in a pathology lab.

FIG. 1 is an exemplary illustration of a probe 100, according to certain embodiments. The probe 100 is an elongated member that is cylindrical in shape and includes a first scanner 102 attached to a distal tip of the probe 100 and a second scanner 104 surrounding a surface of the probe 100 adjacent to the first scanner 102. The probe 100 is made of flexible material, such as plastic, flexible metal, and the like. In addition, the probe 100 is made of a material that is non-magnetic so that the probe 100 can be used in conjunction with other types of medical imaging procedures, such as magnetic resonance imaging (MRI), X-rays, computed tomography (CT) scans, and the like.

In some implementations, the shape of the probe 100 is an elongated square, rectangular, diamond, or any other shape that allows the probe to enter a surgical incision of a body and come in contact with tissues that are under examination. In addition, the first scanner 102 and the second scanner 104 can be any shape that accommodates the shape of the probe 100. In some implementations, more than two scanners are included on the probe 100. According to certain embodiments, the first scanner 102 has a diameter in an inclusive range of 4 millimeters (mm) to 6 mm, such as 5 millimeters (mm) The second scanner 104 has a length in an inclusive range of 10 mm to 30 mm, such as 20 mm, that wraps around an outer surface of the probe 100. The length 106 of the probe 100 is in an inclusive range of 20 centimeters (cm) to 30 cm, and in one implementation is 26 cm.

In some implementations, the first scanner 102 and second scanner 104 include one or more microscopic optical and/or digital sensors, such as the optical system on the OLYMPUS ENF-VH endoscope, that obtain images of the tissue being examined. For a given location of the probe 100, the first scanner 102 and the second scanner 104 are able to obtain images covering approximately a 360-degree field of view. In addition, the one or more sensors can include charged-coupled device (CCD) cameras, complementary metal-oxide semiconductor (CMOS) cameras, and other types of digital cameras.

The first scanner 102 and the second scanner 104 operate using one or more levels of digital and/or optical magnification. In some implementations, the first scanner 102 and the second scanner 104 are included in a telescopic rod lens system that includes one or more lenses for obtaining microscopic images, one or more digital cameras, and fiber optic cables that provide image illumination. In addition, the first scanner 102 and the second scanner 104 of the probe 100 may include one or more bundles of flexible glass fibers to transmit tissue images. In certain embodiments, the magnification level of the first scanner 102 and the second scanner 104 is modified based on digital magnification performed by the one or more digital cameras within the probe 100. For example, the second scanner 104 achieves one or more levels of magnification that include 10×10, 20×10, 40×10, and 100×10 magnifications of the field of view, according to certain embodiments. In one implementation, the one or more digital cameras of the first scanner 102 and second scanner 104 capture the tissue images at one magnification level, and the image magnification is performed by image processing circuitry of the backend system, which will be discussed further herein.

While the description above describes the first scanner and second scanner including fiber optic cables that emit visible light for illumination of the area being examined, the present disclosure also includes other illumination sources. For example, one or more metal halide, mercury, xenon and LEDs may be used to emit light to the illuminate the examination area. The first and second scanners (102 and 104) may include sensors that detect light in the visible spectrum, however these sensors may also include illumination source/filter pairs that detect other types of energy that is not in the visible band, such as infrared source/detector pairs, and ultraviolet source/filter pairs. Furthermore, filter sets may be included in the detectors to match spectral profiles of the light sources in order to isolate selected wavelength bands within a 300 nm to 700 nm range for example. The first and second scanners may also include light sources that provide gentile LED illumination to support inspection of fluorescence signals from the tissue using fluorescence microscopy. Moreover, the tissue under examination may be stained with fluorescent stains (e.g., 4',6-diamidino-2-phenylindole) or, in the case of biological samples, expression of a fluorescent protein (e.g., green fluorescent protein). Alternatively the intrinsic fluorescence of a sample (i.e., autofluorescence) can be used. This approach allows for examination of the distribution of proteins or other molecules of interest.

The probe 100 includes neuro-navigation circuitry 108 that provides intraoperative orientation to the surgeon as the probe 100 is manipulated within the body. According to certain implementations, the neuro-navigation circuitry 108 communicates with a neuro-navigation system, such as MEDTRONIC STEALTHSTATION neuro-navigation system, that includes one or more cameras, reference points, monitors, and circuitry that directs the surgeon navigating the probe to a cerebral tissue location via a wireless or wired connection. In certain embodiments, fiducial markers are placed at one or more reference points in the body of the patient. Fiducial markers are reference objects that are placed inside or outside the body of the patient to assist with locating points of interest within the body, such as a tumor, and determining a size of the tumor. For example, for a brain biopsy where a surgeon is locating a tumor deep within the cerebral tissue, the fiducial markers include one or more MRI-opaque markers that are attached to the skull of the patient. The position of the distal tip of the probe 100 within the cerebral tissue is determined based on the relative location of the probe 100 to the fiducial markers. The probe 100 can also include a solid state compass, accelerometer, and other sensors that detect movement of the probe and can be included in determining the location of the probe 100 within the body.

In certain embodiments, the first scanner 102 and the second scanner 104 are electrically connected to each other by flexible, optical fiber. In addition, the first scanner 102 and second scanner 104 are electrically connected to the backend system via a cord 110. The cord 110 includes an outer sheath that houses at least one optical fiber that transmits the images obtained by the first scanner 102 and the second scanner 104. The outer sheath of the cord 110 is made of a flexible material such as plastic, flexible metal, and the like. In certain embodiments, the outer sheath is made of a material that is non-magnetic so that the probe 100 can be used in conjunction with other imaging equipment, such as MRI. In some implementations, the probe 100 includes circuitry to allow the probe 100 to wirelessly communicate with the backend system, and the cord 110 may not be included.

Figure 2:
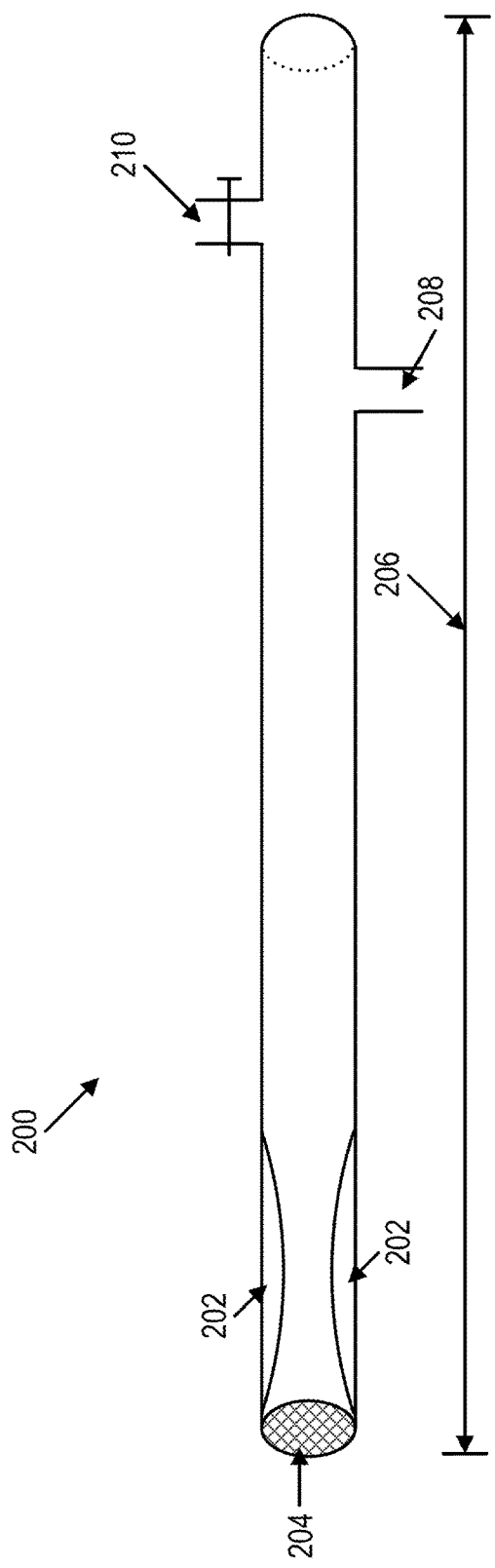
FIG. 2 is an exemplary illustration of an outer casing for a probe, according to certain embodiments.

FIG. 2 is an exemplary illustration of an outer casing 200 for the probe 100, according to certain embodiments. The outer casing length 206 is approximately 20 cm extending from a distal tip where mesh plate 204 is attached to a proximal tip. The mesh plate 204 is made of a flexible, permeable material, such as silicone mesh, that covers the first scanner 102 and allows the tissue being examined to be pulled into the outer casing 200 to be examined by the probe 100. In some aspects, the mesh plate 204 is approximately circular in shape and has a larger diameter than the diameter of the first scanner 102. For example, for the probe 100 with a first scanner 102 that is approximately 5 mm in diameter, the mesh plate 204 of the outer casing 200 is in an inclusive range of 6 mm to 8 mm in diameter, and in one implementation is 7 mm.

In some implementations, inner walls of the distal end of the outer casing 200 include at least one balloon 202 that inflates and deflates to draw tissue being examined through the mesh plate 204 to be examined by the first scanner 102 and the second scanner 104. For example, to inflate the at least one balloon 202, air is introduced into the at least one balloon 202 through the air connection port 208 in the outer casing 200, which creates a pressure differential that draws the tissue into the outer casing 200 and within viewing range of the first scanner 102 and the second scanner 104. In some implementations, the air connection port is in an inclusive range of 30 mm to 50 mm from the proximal end of the outer casing 200, such as 40 mm. The air connection port 208 connects to air supply sources, such as medical gas supply systems in a hospital, and may include one or more adapter fittings to receive air from one or more types of air supply sources. To deflate the at least one balloon 202, air is released via the air connection port 208.

The outer casing 200 also includes a suction connection 210 that is in an inclusive range of 10 mm to 30 mm from the proximal end of the outer casing 200, such as 20 mm, according to certain embodiments. The suction connection 210 allows a suction tube to be connected to the outer casing 200 to remove fluid that may obscure the tissue being examined by the first scanner 102 and the second scanner 104.

Figure 3:
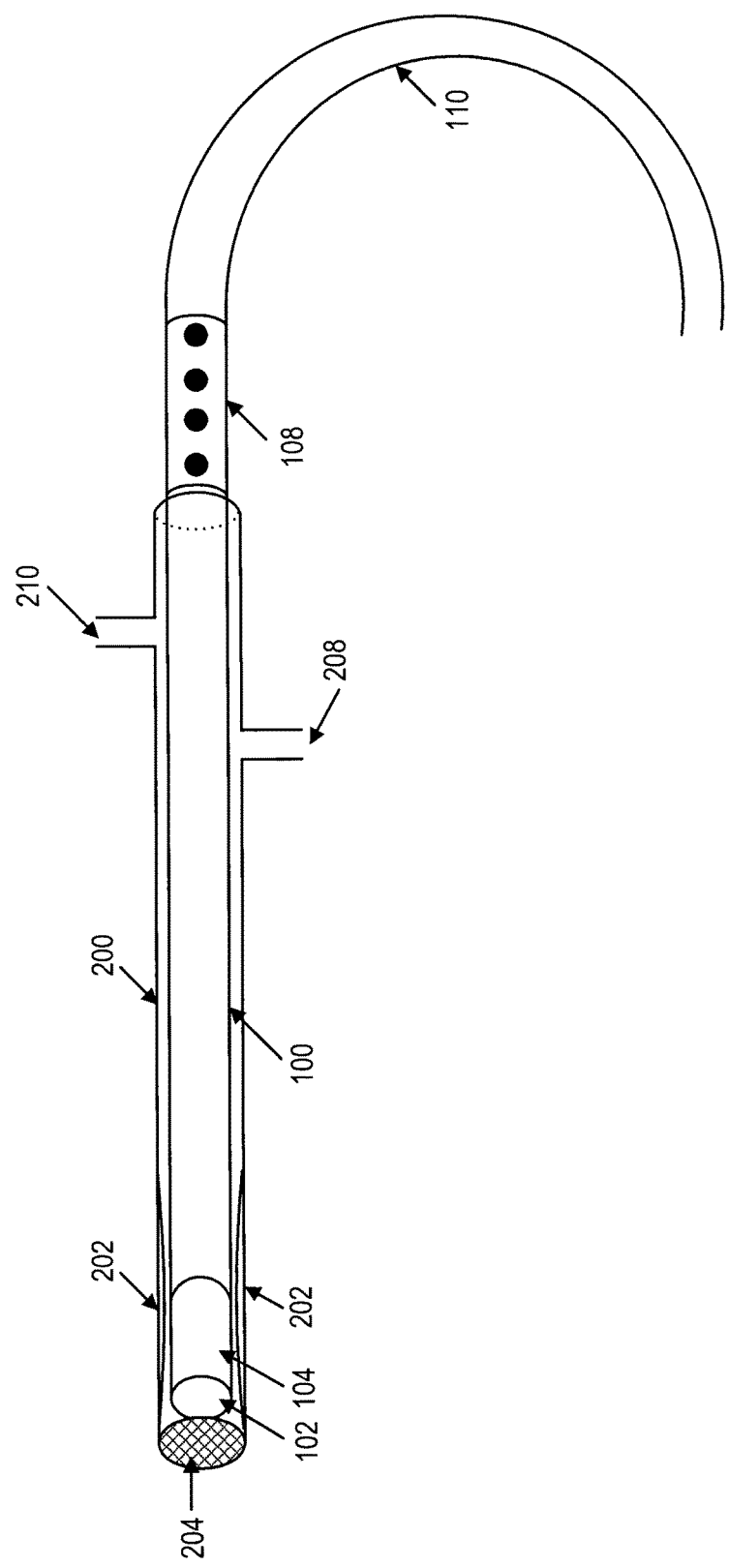
FIG. 3 is an exemplary illustration of an outer casing surrounding a probe, according to certain embodiments.

FIG. 3 is an exemplary illustration of an outer casing 200 surrounding a probe 100, according to certain embodiments. The probe 100 is inserted into the outer casing 200 so that the first scanner 102 at the distal tip of the probe 100 is located adjacent to the mesh plate 204 at the distal end of the outer casing 200. In some implementations, the outer casing 200 covers the length of the probe 100 from the first scanner 102 up to the neuro-navigation circuitry 108.

The probe 100, surrounded by the outer casing 200, is inserted into the area of the body where the tissue is being examined, such as into the cerebral tissue. The medical professional, such as a surgeon, advances the probe 100 into the body through a surgical incision or bodily orifice and is guided by the neuro-navigation circuitry 108 that performs intraoperative orientation to determine the location of the tissue being examined by the probe 100. When the probe 100 is in a desired location for tissue examination, the medical professional applies pressure to push the tissue through the mesh plate 204 in order to be in viewing range of the first scanner 102. In some implementations, suction is applied via the suction connection 210 to attract the tissue to the first scanner 102. The first scanner 102 obtains one or more images of the tissue cells, which are transmitted to the backend system for digital staining and identification, as will be discussed further herein.

In certain embodiments, additional magnification of the tissue cells is performed by the second scanner 104. The at least one balloon 202 is inflated by introducing air into the air connection port 208. As the at least one balloon 202 inflates, a pressure differential is created, and the tissue cells are drawn to the surface of the second scanner 104. The second scanner 104 obtains one or more images of the tissue cells, which are transmitted to the backend system for digital staining and identification, as will be discussed further herein. When the medical professional has completed examination of the tissue with the probe 100, the at least one balloon 202 is deflated by allowing the air in the at least one balloon to escape from the outer casing 200 via the air connection port 208. In some implementations, the first scanner 102 and the second scanner 104 of one or more probes perform unequal amounts of magnification, and the medical professional can change out the probes based on the desired amount of magnification.

Figure 4:
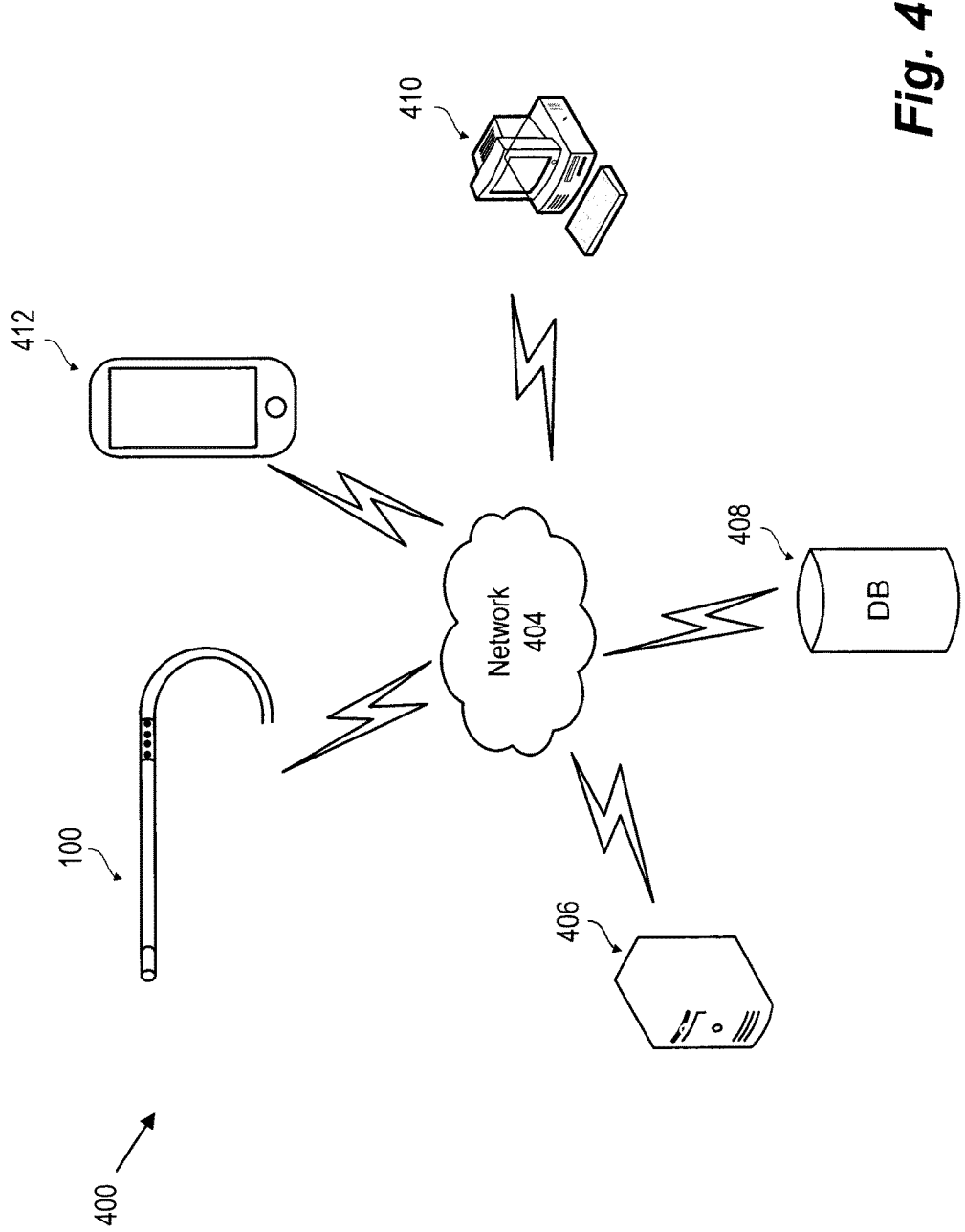
FIG. 4 is an exemplary illustration of a histopathology system, according to certain embodiments.

FIG. 4 is an exemplary illustration of a histopathology system 400, according to certain embodiments. The probe 100 is connected to a backend system, which includes a server 406, database 408, computer 410, and mobile device 412 via a network 404. In some embodiments, more than one probe 100 is included in the histopathology system 400. As such, the terms referring to the one or more than one probe 100 can be used interchangeably. The probe 100 can have a wired or wireless connection with the backend system.

The server 406 represents one or more servers connected to the computer 410, the database 408, the mobile device 412, and the probe 100 via the network 404. The server 406 includes processing circuitry that executes one or more software processes related to capturing tissue images via the probe 100, performing digital staining procedures, and matching the tissue images obtained by the probe 100 to the tissue samples of the histopathological library stored in the database 408. The processing circuitry of the server 406 also executes one or more software processes related to implementing augmented reality features to the tissue examination procedure 500. Details regarding the software processes performed by the processing circuitry of the server 406 will be discussed further herein.

The computer 410 acts as a client device that is connected to the server 406, the database 408, the mobile device 412, and the probe 100 via the network 404. In some implementations, the computer 410 is located in the operating room where the medical professional performing the tissue examination procedure 500 can view the monitor of the computer 410 as the probe 100 acquires the tissue images and provide inputs and amplifying information via an interface. In certain embodiments, the computer 410 is in a pathology lab outside the operating room where the tissue examination procedure 500 is performed, and pathologists view the images on the computer 410 and provide feedback regarding tissue images obtained by the probe 100.

The database 408 represents one or more databases connected to the computer 410, the server 406, the mobile device 412, and the probe 100 via the network 404. In some implementations, a histopathological library is stored in the database 408 that includes a plurality of types of healthy and diseased tissue samples that are compared to the tissue being examined. For example, when the tissue images obtained by the first scanner 102 and second scanner 104 are transmitted to the backend system, the processing circuitry of the server 406 performs a matching algorithm to determine if the tissue being examined matches any of the tissue samples in the histopathological library. Details regarding the matching algorithm are discussed further herein.

The mobile device 412 represents one or more mobile devices connected to the computer 410, the server 406, the database 408, and the probe 100 via the network 404. The network 404 represents one or more networks, such as the Internet, connecting the computer 410, the server 406, the database 408, the mobile device 412, and the probe 100. The network 404 can also represent any other type of wireless network such as WI-FI, BLUETOOTH, cellular networks including EDGE, 3G and 4G wireless cellular systems, or any other wireless form of communication that is known.

As would be understood by one of ordinary skill in the art, based on the teachings herein, the mobile device 412 or any other external device could also be used in the same manner as the computer 410 to view the tissue images obtained by the probe 100 as well as the matched tissues from the histopathological library. For example, as the surgeon advances the probe 100 in to the tissue being examined and obtains images of the tissue via the first scanner 102 and the second scanner 104, a pathologist in the operating room or in a laboratory views the images obtained by the probe 100 and one or more matched tissue images at an interface at the computer 110 or via an application on the mobile device 112. The pathologist can then select one or more of the matched tissue images as a most likely candidate for the type of tissue being examined and can add annotations to the images obtained by the probe 100.

The information input by the pathologist at the computer 410 or mobile device 412 is received by the server 406. The server 406 transmits the information input by the pathologist to the computer 410 and/or mobile device 412 of the surgeon in the operating room. The information input by the pathologist and/or surgeon is also stored in the database 408 and can be accessed during post-operative assessments as well as future surgeries. Details regarding the processes performed by the histopathology system 400 are discussed further herein.

In some implementations, the histopathology system 400 performs augmented reality processes in which the surgeon documents details of the surgery via notes, images, video, and the like. The details of the surgery are associated with the location of the probe 100 within the body and are stored in the backend system so that the details of the surgery can be accessed by the surgeon in future surgeries. For example, if the processing circuitry of the server 406 matches the tissue images obtained by the probe to cancerous tumor samples in the histopathological library, the surgeon can record amplifying information, such as the size of the tumor, characteristics of the cancerous cells, characteristics of the healthy cerebral cells, and location of the cancerous cells within the brain. During future surgeries, as the probe 100 approaches the locations of where notes have been documented, the histopathology system provides the surgeon with the amplifying information that has been saved so that the surgeon can determine change in size of the cancerous tumor, effectiveness of treatments, and the like. Details of the documentation of amplifying information are discussed further herein.

Figure 5:
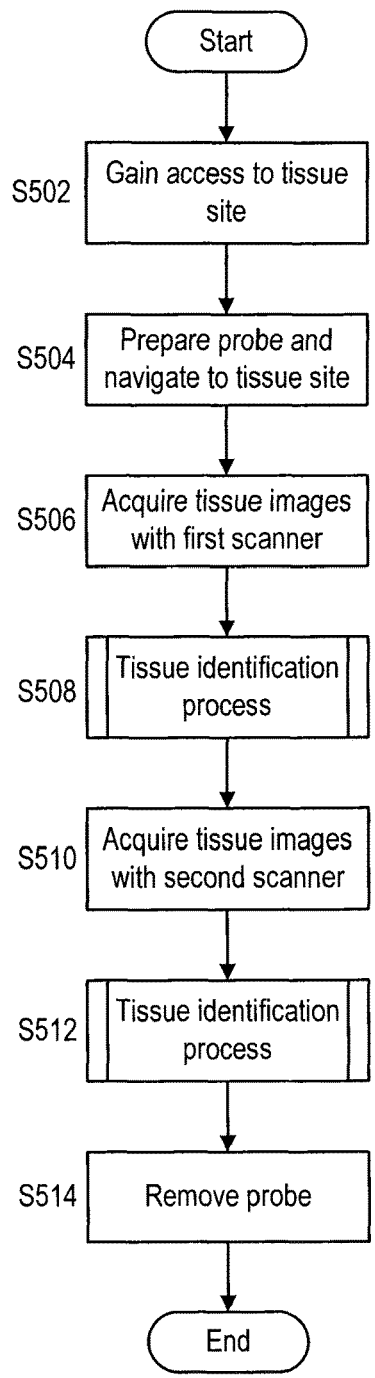
FIG. 5 is an exemplary flowchart for performing a real time tissue identification process, according to certain embodiments.

FIG. 5 is an exemplary flowchart for performing a real time tissue examination procedure 500, according to certain embodiments. At step S502, the medical professional, such as the surgeon, gains access to the site of the tissue being examined by the probe 100. For example, during surgery to locate and/or remove a brain tumor, the surgeon gains access to the cerebral tissue by making at least one surgical incision. In some implementations, the medical professional gains access to the tissue site through a natural orifice of the patient's body. For example, if tissue of the digestive system is being examined, the probe 100 is advanced through the patient's mouth or anus depending on the section of the digestive system being examined.

At step S504, the probe 100 is prepared for the tissue examination procedure 500 and navigated to the site of the tissue being examined. The medical professional selects the probe 100 that will be used based on the amount of magnification by the first scanner 102 and the second scanner 104. For example, a probe 100 with a largest amount of magnification may be selected to examine some types of neurons that are smaller and more densely populated than other types of neurons. The selected probe 100 is inserted into the outer casing 200 so that the first scanner 102 at the distal tip of the probe 100 is located adjacent to the mesh plate 204 at the distal end of the outer casing 200.

The medical professional inserts the probe 100 through the incision or orifice and is guided to the location of the tissue being examined based on a position determination made by the neuro-navigation circuitry 108. In addition, the first scanner 102 and second scanner 104 obtain images as the probe 100 is guided to the location of the tissue examination, and the medical professional guiding the probe 100 views the images on a display that is connected to the computer 610. In some aspects, the processing circuitry of the server 406 determines that the probe 100 has reached the location for the tissue examination based on the location output by the neuro-navigation circuitry 108.

In some implementations, the processing circuitry of the server 406 is configured to implement augmented reality processes that save notes dictated and/or recorded by the medical professional and images obtained by the probe 100 along with a corresponding location of the probe 100 during the tissue examination. The notes and/or images are saved in the database 408 and accessed during future tissue examination procedures. For example, based on the location of the probe 100 determined by the neuro-navigation circuitry 108, the processing circuitry of the server 406 outputs the notes and/or images that correspond to the locations of the probe 100 from previous tissue examination procedures for the patient.

At step S506, when the probe 100 has reached the location of the tissue being examined, one or more tissue images are captured by the first scanner 102. The medical professional applies pressure to push the tissue through the mesh plate 204 of the outer casing 200 in order to be in viewing range of the first scanner 102. In some implementations, suction is applied via the suction connection 210 to attract the tissue to the first scanner 102, and the first scanner 102 obtains one or more images of the tissue cells. In some implementations, the medical professional performing the tissue examination procedure 500 indicates that the probe is in the location for tissue examination by pushing a button on the probe 100, clicking a mouse, verbal input, touching a touchscreen on the computer, and the like. In certain embodiments, images are obtained by the first scanner 102 at a predetermined sampling rate or at a rate indicated by the medical professional.

In certain embodiments, the medical professional can adjust the magnification level of the first scanner 102 based on the size, density, and clarity of cells in the images obtained by the second scanner 104. As the first scanner 102 captures the tissue images, the medical professional can view the images on a monitor and can provide notes and/or annotations related to the tissue being examined. The notes and annotations can be saved in the patient's medical record as well as in the database 408 in order to be accessed during future surgeries and/or tissue examination procedures. In some implementations, step S506 may be omitted from the tissue examination procedure 500 if the medical professional determines that images obtained by the second scanner 104 in step S510 are sufficient for performing proper identification of the tissue.

At step S508, the processing circuitry of the server 406 performs a tissue identification process that will be discussed further herein. At step S510, one or more images are obtained with the second scanner 104. In some implementations, the images are obtained with the second scanner 104 before images are obtained with the first scanner 102. In certain embodiments, additional magnification of the tissue cells is performed by the second scanner 104. The at least one balloon 202 is inflated by introducing air into the air connection port 208. As the at least one balloon 202 inflates, a pressure differential is created, which draws the tissue cells to the surface of the second scanner 104, and the tissue images are captured. In some implementations, the medical professional performing the tissue examination procedure 500 indicates that the probe is in the location for tissue examination by pushing a button on the probe 100, clicking a mouse, verbal input, touching a touchscreen on the computer, and the like. In certain embodiments, images are obtained by the second scanner 104 at a predetermined sampling rate or at a rate indicated by the medical professional.

The medical professional can adjust the magnification level of the second scanner 104 based on the size, density, and clarity of cells in the images obtained by the second scanner. For example, in certain embodiments, the second scanner 104 can perform one or more levels of magnification that include 10×10, 20×10, 40×10, and 100×10 magnifications of the field of view. As the second scanner 104 captures the tissue images, the medical professional views the images on the monitor of the computer 410 and provides amplifying information, such as notes and/or annotations related to the tissue being examined. The amplifying information is saved in the patient's medical record as well as in the database 408 in order to be accessed during future surgeries and/or tissue examination procedures. In addition, step S510 may be omitted from the tissue examination procedure 500 if the medical professional determines that the tissues identified from the images obtained by the first scanner are sufficient for the procedure being performed.

At step S512, the processing circuitry of the server 406 performs the tissue identification process that will be discussed further herein. At step S514, the probe is removed from the tissue site when the medical professional has obtained a desired amount of tissue images with the probe 100. When the medical professional has completed examination of the tissue with the probe 100, the at least one balloon 202 is deflated by allowing the air in the at least one balloon to escape from the outer casing 200 via the air connection port 208, and the probe 100 is removed from the body of the patient via the surgical incision or the bodily orifice.

Figure 6:
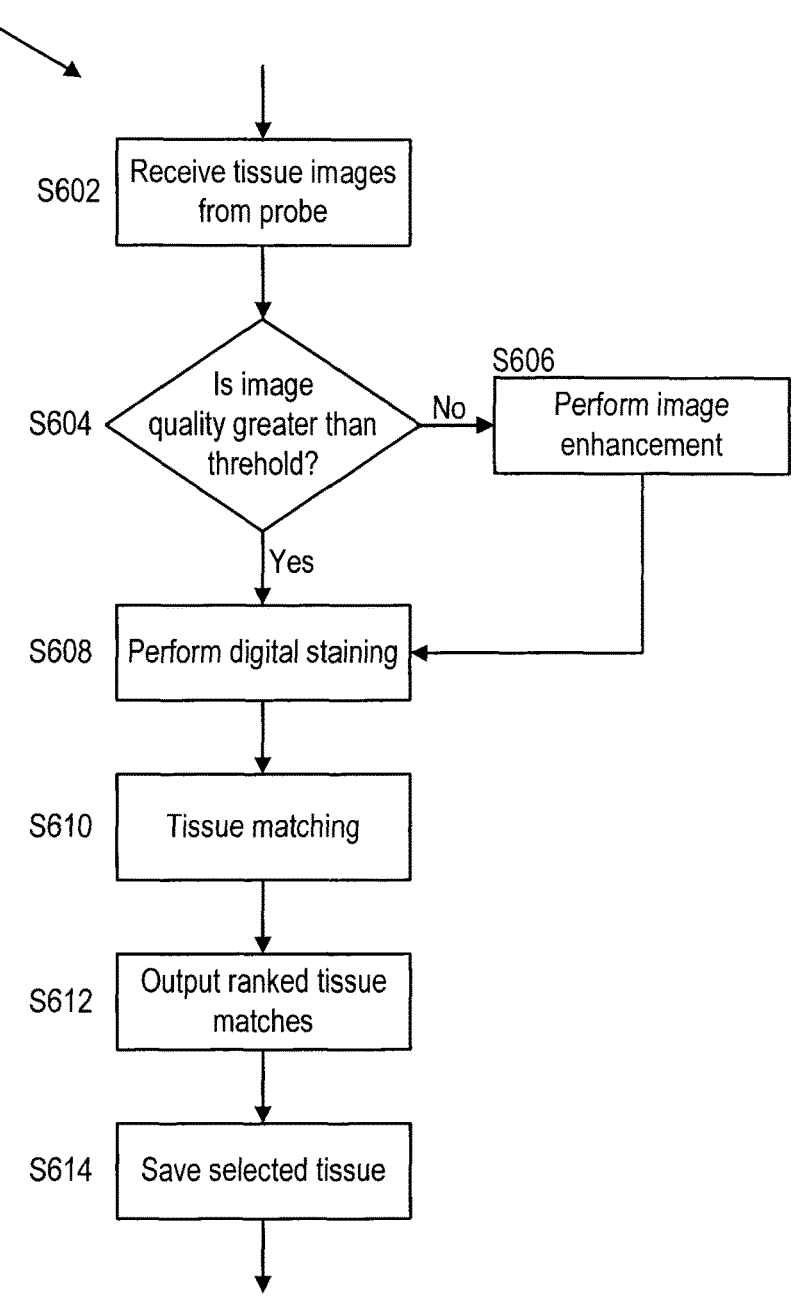
FIG. 6 is an exemplary flowchart for a tissue identification process, according to certain embodiments.

FIG. 6 is an exemplary flowchart for the tissue identification process of steps S508 and S512, according to certain embodiments. At step 5602, the processing circuitry of the server 406 receives the one or more tissue images obtained by the probe 100 in the tissue examination procedure 500. The one or more unprocessed images are stored in database 408 and can be accessed in order to perform non-real time histopathology analysis. In some implementations, the processing circuitry of the server 406 performs digital magnification of the one or more tissue images obtained by the probe 100.

At step S604, it is determined whether the quality of the images being processed is greater than a predetermined threshold. In certain embodiments, the images received from the probe 100 are assigned a quality factor, such as a percentage of an approximate maximum image quality, based on overall clarity, detection of cell boundaries and cell components based on a shape of the cells being analyzed, and likelihood that the tissue will be correctly matched at step S610. In one implementation the predetermined threshold for the tissue image quality is set to 75% but can be modified to be any percentage based on examination conditions, type of tissue being examined, and the like. If the quality of the images obtained by the probe 100 is greater than the predetermined threshold, resulting in a "yes" at step S604, then step S608 is performed. Otherwise, if the quality of the images obtained by the probe is less than the predetermined threshold, resulting in a "no" at step S604, then step S606 is performed.

At step S606, if it is determined at step S604, that the quality of the images obtained by the probe 100 is less than the predetermined threshold, the images are enhanced to increase the quality. In some implementations, edge detection filters are applied to the images, and the contrast of the pixels of the boundaries of the cells and cell components is increased. If the quality of the images after the image enhancement is less than the predetermined threshold, then processing circuitry of the server 406 outputs an alert to the medical professional performing the tissue examination that the image quality is too low to accurately identify the tissue being examined. The alert is output via the computer 410 in the operating room or via the mobile device 412, so that the medical professional can acquire additional tissue images via the first scanner 102 and/or the second scanner 104.

At step S608, digital stains are applied to the tissue images obtained by the probe 100. As used herein, the terms "stain" and "staining" can include without limitation staining with a dye or a stain, immunohistochemical staining, aptamer staining, tagging, chemical staining, antibody staining, or any other alteration to a tissue sample. Digital staining includes applying the one or more staining techniques to the tissue being examined with software processes that modify one or more pixels of the tissue images to highlight cell components, abnormalities, and the like. The processing circuitry of the server 406 determines the one or more digital stains to be applied to the tissue images based on the type tissue, type of diagnosis being performed, and the like. In some implementations, the medical professional manually inputs the one or more digital stains to be applied to the tissue images.

At step S610, a tissue matching algorithm is executed to match the tissue images obtained by the probe 100 to one or more tissue samples in the histopathological library. In certain embodiments, the processing circuitry executes one or more matching and/or pattern recognition algorithms to determine that the tissue being examined shares one or more features with at least one tissue sample in the histopathological library. For example, when determining if brain tissue cells are cancerous, the processing circuitry of the server 406 compares the brain tissue cells obtained by the probe 100 to cancerous and non-cancerous brain tissue samples stored on the histopathological library. If the brain tissue images share more common features with the cancerous tissue samples than the non-cancerous tissue samples, then the processing circuitry may determine that the brain tissue being examined by the probe 100 may be cancerous. In some implementations, features of the tissue images are converted to feature vectors that are compared to feature vectors of the tissue samples in the histopathological library to determine one or more possible matches.

At step S612, the server 406 outputs a predetermined number of highest ranking matches determined at step S610. For example, the medical professional can indicate at the computer 410 for the server to output the top three tissue samples from the histopathological library that most closely match the tissue being examined by the probe 100 based on the matching or pattern recognition algorithm implemented by the processing circuitry. In some implementations, the highest ranking matches are determined based on a number or percentage of common features shared between the tissue images obtained by the probe 100 and the tissue samples of the histopathological library. In some aspects, the feature vectors of the tissue images obtained by the probe 100 are compared to the feature vectors of the tissue samples in the histopathological library, and the server 406 outputs the types of tissue with a predetermined number of matching features. The medical professional, such as the surgeon or pathologist, then selects the most likely tissue sample candidate from the highest ranking matches output by the server 406.

If the processing circuitry is unable to match the tissue images obtained by the probe 100 to the tissue samples of the histopathological library due to having approximately zero shared features between the tissue images and the tissue samples, the server 406 outputs an alert to the medical professional via the computer 410 or mobile device 112. In addition, if the processing circuitry outputs zero tissue matches, the medical professional can manually indicate for the processing circuitry to perform the digital staining of step S608 with a different digital staining technique and repeat the matching algorithm of step S610. The medical professional can also view the digitally stained images on the monitor of the computer 410 or the mobile device 112 and determine the type and characteristics of the tissue.

At step S614, the digitally stained tissue images are stored in the database 408 along with the amplifying information provided by the medical professional during the tissue examination procedure 500. FIG. 7 is an exemplary illustration of a matched tissue image with amplifying information, according to certain embodiments. In one implementation, the probe 100 is used to obtain images of cerebral tissue to determine a location and size of a brain tumor. The one or more matched tissue images determined through the tissue identification process of steps S508 and S512 include patient identification information, such as a name, identification number, date of procedure, name of surgeon, and type of procedure being performed. The matched tissue images also include the type of tissue identified along with notes and/or annotations made by the medical professional that may include size of tumor, location of the tumor, amount of magnification with scanner, type of digital stain used, and the like. The matched tissue images and the amplifying information is then stored in the database 408 with the patient's medical record and can be accessed during future tissue examination procedures to assess the success of treatments and monitor any changes in the tissue.

According to certain embodiments, the histopathology system 400 performs real time tissue identification, which allows medical professionals to provide immediate feedback regarding disease diagnoses, which allows the medical professionals to administer timely care to patients. By using the probe 100 to locate and obtain images of the tissue and the processing circuitry of the server 406 to digitally stain and identify the tissue, identification of the tissue may not require obtaining an actual tissue sample that is analyzed in a laboratory. In addition, the medical professional, such as a surgeon, can take action to remove tissue that is identified as diseased without having to perform an additional surgery, which may cause additional stress to the patient and introduce complications. The histopathology system 400 can be implemented in medical disciplines where diagnosing cells as healthy or diseased in real time may improve an outcome for a patient, such as spinal and cerebral surgery, renal surgery, gynecological surgery, hepatic surgery, general surgery, and the like.

A hardware description of the server 406 according to exemplary embodiments is described with reference to FIG. 8. In some implementations, the hardware described by FIG. 8 also applies to the computer 410 or mobile device 412 to perform the processes as described previously herein. Implementation of the processes of the histopathology system 400 on the hardware described herein allows for increased speed and accuracy of pathology diagnoses. The server 406 includes a CPU 800 that perform the processes described herein. The process data and instructions may be stored in memory 802. These processes and instructions may also be stored on a storage medium disk 804 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the server 406 communicates, such as the computer 410.

Further, the claimed advancements may be provided as a utility application, background daemon, or component of an operating system, or combination thereof, executing in conjunction with CPU 800 and an operating system such as Microsoft Windows 7, UNIX, Solaris, LINUX, Apple MAC-OS and other systems known to those skilled in the art.

CPU 800 may be a Xenon or Core processor from Intel of America or an Opteron processor from AMD of America, or may be other processor types that would be recognized by one of ordinary skill in the art. Alternatively, the CPU 800 may be implemented on an FPGA, ASIC, PLD or using discrete logic circuits, as one of ordinary skill in the art would recognize. Further, CPU 800 may be implemented as multiple processors cooperatively working in parallel to perform the instructions of the inventive processes described above.

Figure 8:
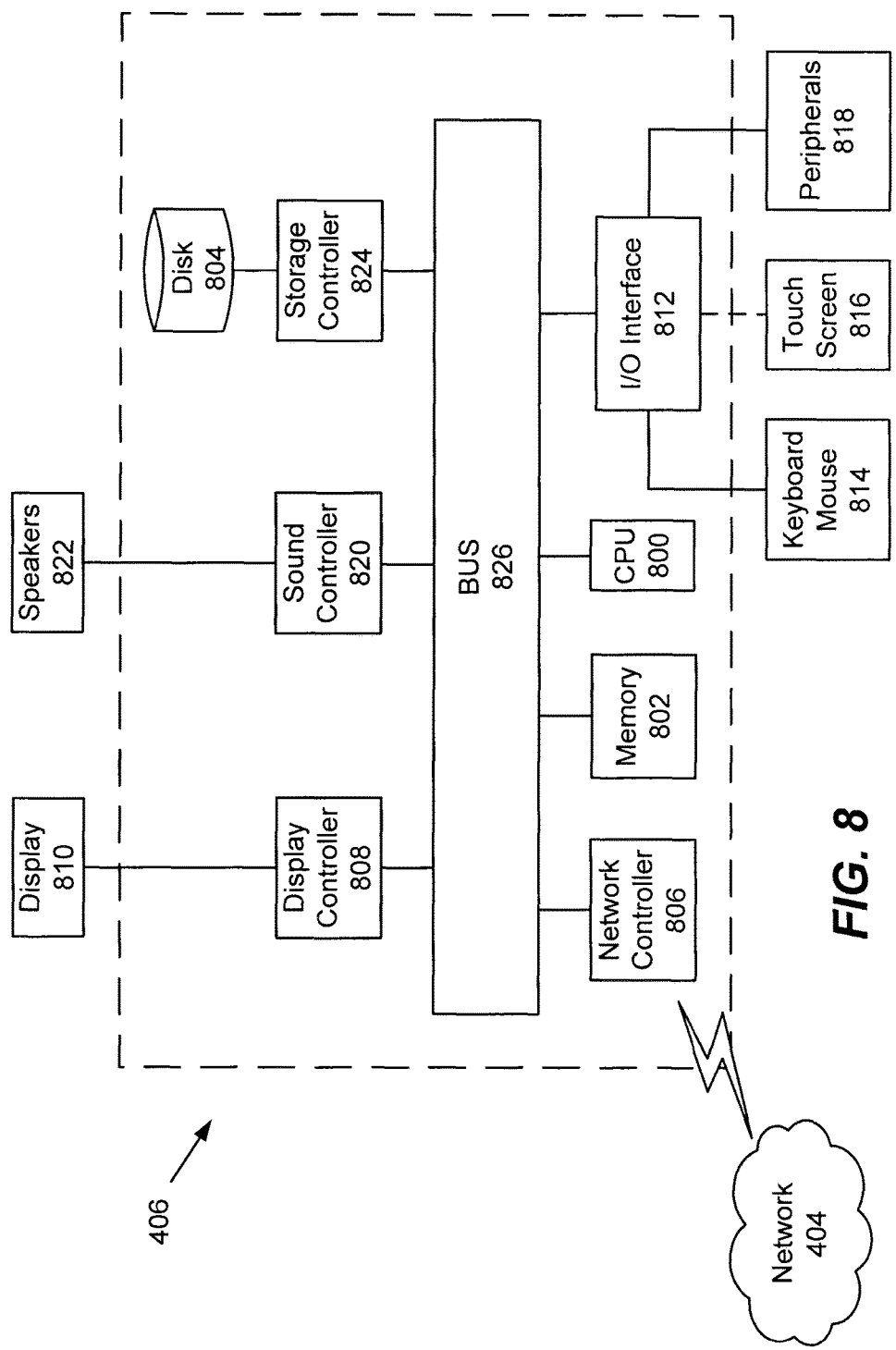
FIG. 8 illustrates a non-limiting example of a server for an emergency response system, according to certain embodiments.

The server 406 in FIG. 8 also includes a network controller 806, such as an Intel Ethernet PRO network interface card from Intel Corporation of America, for interfacing with network 404. As can be appreciated, the network 404 can be a public network, such as the Internet, or a private network such as an LAN or WAN network, or any combination thereof and can also include PSTN or ISDN sub-networks. The network 404 can also be wired, such as an Ethernet network, or can be wireless such as a cellular network including EDGE, 3G and 4G wireless cellular systems. The wireless network can also be Wi-Fi, Bluetooth, or any other wireless form of communication that is known.

The server 406 further includes a display controller 808, such as a NVIDIA GeForce GTX or Quadro graphics adaptor from NVIDIA Corporation of America for interfacing with display 810 of the computer 410, such as a Hewlett Packard HPL2445w LCD monitor. A general purpose I/O interface 812 at the server 406 interfaces with a keyboard and/or mouse 814 as well as a touch screen panel 816 on or separate from display 810. General purpose I/O interface 812 also connects to a variety of peripherals 818 including printers and scanners, such as an OfficeJet or DeskJet from Hewlett Packard.

A sound controller 820 is also provided in the server 406, such as Sound Blaster X-Fi Titanium from Creative, to interface with speakers/microphone 822 thereby providing sounds and/or music. The general purpose storage controller 824 connects the storage medium disk 804 with communication bus 826, which may be an ISA, EISA, VESA, PCI, or similar, for interconnecting all of the components of the server 406. A description of the general features and functionality of the display 810, keyboard and/or mouse 814, as well as the display controller 808, storage controller 824, network controller 806, sound controller 820, and general purpose I/O interface 812 is omitted herein for brevity as these features are known.

In other alternate embodiments, processing features according to the present disclosure may be implemented and commercialized as hardware, a software solution, or a combination thereof. Moreover, instructions corresponding to the tissue identification process of steps S508 and S512 in accordance with the present disclosure could be stored in a thumb drive that hosts a secure process.

A number of implementations have been described. Nevertheless, it will be understood that various modifications may be made without departing from the spirit and scope of this disclosure. For example, preferable results may be achieved if the steps of the disclosed techniques were performed in a different sequence, if components in the disclosed systems were combined in a different manner, or if the components were replaced or supplemented by other components. The functions, processes and algorithms described herein may be performed in hardware or software executed by hardware, including computer processors and/or programmable circuits configured to execute program code and/or computer instructions to execute the functions, processes and algorithms described herein. Additionally, an implementation may be performed on modules or hardware not identical to those described. Accordingly, other implementations are within the scope that may be claimed.

The invention claimed is:

1. A histopathology system comprising:
an elongated, cylindrical probe comprising
one or more scanners adjacent to a distal end of the probe and configured to capture a digital image of a tissue, and
neuro-navigation circuitry configured to navigate the probe to a tissue examination site:
an outer casing into which the probe is inserted having a mesh plate integrally formed at a distal tip of the outer casing through which the tissue is drawn, and
at least one balloon attached to an inner surface of the outer casing, wherein the at least one balloon is configured to be inflated and, when inflated, creates a pressure differential that draws the tissue into viewing range of the one or more scanners; and
at least one server comprising processing circuitry, the processing circuitry configured to
digitally stain the digital of the image of the tissue obtained by the one or more scanners to produce a digitally stained tissue image, and
match the digitally stained tissue image to one or more stored images of tissue samples.

2. The system of claim 1, wherein the one or more scanners includes a first scanner at a face of the distal end of the probe, the first scanner having a diameter in an inclusive range of 4 to 6mm.

3. The system of claim 1, wherein the one or more scanners includes a second scanner wrapped around an outer surface of the probe, the second scanner having a longitudinal length in an inclusive range from 10 to 30 mm.

4. The system of claim 1, wherein the one or more scanners are configured to obtain the digital image of the tissue, the digital image covering a 360-degree field of view.

5. The system of claim 1, wherein the mesh plate of the outer casing has a circular shape with a diameter in an inclusive range of 6 mm to 8 mm.

6. The system of claim 5, wherein the mesh plate comprises silicone.

7. The system of claim 1, wherein the outer casing includes an air connection port through which air is introduced into the outer casing to inflate the at least one balloon.

8. The system of claim 7, wherein the at least one balloon is deflated by allowing the air from the at least one balloon to escape through the air connection port.

9. The system of claim 7, wherein the air connection port is positioned in an inclusive range from 30 mm to 50 mm from a proximal end of the outer casing.

10. The system of claim 1, wherein the outer casing includes a suction connection positioned in an inclusive range from 10 mm to 30 mm from a proximal end of the outer casing.

11. The system of claim 1, wherein the probe is in an inclusive range of 20 cm to 30 cm in length, and the outer casing is in an inclusive range of 15 cm to 25 cm in length.

12. The system of claim 1, wherein the one or more scanners magnify the tissue being examined by one or more predetermined magnification levels.

13. The system of claim 1, wherein the processing circuitry of the at least one server is further configured to output amplifying information obtained from the neuro-navigation circuitry during tissue examination procedures based on a location of the probe configured to be inserted within a body of a patient.

14. The system of claim 13, further comprising an external device comprising a processing circuitry configured to receive user notes,
wherein the amplifying information includes at least one of patient identification information, the location of the probe, the one or more stored images of tissue samples, and user notes entered at the external device.

15. The system of claim 1, wherein the processing circuitry of the at least one server is further configured to determine that a quality of the digital image of the tissue is greater than a predetermined threshold.

16. The system of claim 1, wherein the processing circuitry of the at least one server is further configured to output a predetermined number of stored images of tissue samples that match with the digitally stained tissue image.

17. The system of claim 16, further comprising an external device comprising a processing circuitry configured to receive an input from a user,
wherein the processing circuitry of the at least one server is further configured to receive a selection at the external device of a stored image from the predetermined number of stored images of tissue samples.

18. A method for examining tissue comprising:
inserting an elongated, cylindrical probe into an outer casing so that a mesh plate of the outer casing covers a distal end of the probe;
navigating the probe to a tissue examination site via neuro-navigation circuitry;
applying pressure to the tissue examination site to push tissue through the mesh plate;
creating a pressure differential that draws the tissue into viewing range of one or more scanners by inflating at least one balloon attached to an inner surface of the outer casing; and
capturing digital images of the tissue via the one more scanners.

19. A probe for examining tissue, the probe comprising:
one or more scanners connected to a distal end of the probe and configured to capture digital images of tissue, and
neuro-navigation circuitry configured to navigate the probe to a tissue examination site;
an outer casing into which the probe is inserted having a mesh plate integrally formed at a distal tip of the outer casing through which a tissue is drawn, and
at least one balloon attached to an inner surface of the outer casing, wherein the at least one balloon is configured to be inflated and, when inflated, creates a pressure differential that draws the tissue into viewing range of the one or more scanners.

* * * * *